US010451217B2

United States Patent
Ravalitera et al.

(10) Patent No.: US 10,451,217 B2
(45) Date of Patent: Oct. 22, 2019

(54) MEDICAL SUSPENSION DEVICE COMPRISING AN OFFSET ARM

(71) Applicant: Maquet SAS, Ardon (FR)

(72) Inventors: Pierre Ravalitera, Ardon (FR); Bertrand Guilleminot, Ardon (FR); Gregory Senelier, Ardon (FR)

(73) Assignee: Maquet SAS (FR)

( * ) Notice: Subject to any disclaimer, the term of this patent is extended or adjusted under 35 U.S.C. 154(b) by 0 days.

(21) Appl. No.: 15/777,027

(22) PCT Filed: Jan. 18, 2017

(86) PCT No.: PCT/FR2017/050102
§ 371 (c)(1),
(2) Date: Aug. 9, 2018

(87) PCT Pub. No.: WO2017/125677
PCT Pub. Date: Jul. 27, 2017

(65) Prior Publication Data
US 2018/0372270 A1   Dec. 27, 2018

(30) Foreign Application Priority Data

Jan. 19, 2016  (FR) ..................... 16 50394

(51) Int. Cl.
*F16M 13/02* (2006.01)
*F16M 11/20* (2006.01)
(Continued)

(52) U.S. Cl.
CPC .......... *F16M 13/027* (2013.01); *A61B 90/35* (2016.02); *A61B 90/50* (2016.02); *A61G 12/004* (2013.01);
(Continued)

(58) Field of Classification Search
CPC .. F16M 13/027; F16M 11/2014; F16M 11/24; F16M 11/2092; F16M 2200/063; A61B 90/35; A61B 90/50; A61G 12/004
(Continued)

(56) References Cited

U.S. PATENT DOCUMENTS 6,012,821 A * 1/2000 Yeaney .................. F16M 11/10
248/325
6,328,458 B1 * 12/2001 Bell ....................... F16M 11/10
362/288
(Continued)

FOREIGN PATENT DOCUMENTS

EP   1 239 805 A1   9/2002
EP   1442246 A1     8/2004
(Continued)

OTHER PUBLICATIONS

JP Office Action dated Jun. 25, 2019 issued by the Japanese Patent Office in corresponding JP Application No. 2018-527782, along with English summary (previously submitted with EFS ID #36678253).
(Continued)

*Primary Examiner* — Muhammad Ijaz
(74) *Attorney, Agent, or Firm* — Ware, Fressola, Maguire & Barber LLP

(57) ABSTRACT

A suspension device making it possible to suspend items of equipment (7, 7') under a support structure comprises an anchor bracket (2) designed to be anchored axially to the support structure, two distribution arms (9, 10, 9', 10') that are adjustable up and down and that are designed to carry the items of equipment (7, 7'), and that are connected to the anchor bracket (2) via pivot articulations (11, 11'), each of which is offset from the anchor bracket (2) via a stationary offsetting arm (8, 8'; 8").

20 Claims, 2 Drawing Sheets

(51) Int. Cl.
*F16M 11/24* (2006.01)
*A61G 12/00* (2006.01)
*A61B 90/50* (2016.01)
*A61B 90/35* (2016.01)

(52) U.S. Cl.
CPC ..... *F16M 11/2014* (2013.01); *F16M 11/2092* (2013.01); *F16M 11/24* (2013.01); *F16M 2200/063* (2013.01)

(58) Field of Classification Search
USPC ...... 248/124.1, 278.1, 284.1, 313, 317, 323, 248/324
See application file for complete search history.

(56) References Cited

U.S. PATENT DOCUMENTS

| | | | | |
|---|---|---|---|---|
| 6,364,268 | B1* | 4/2002 | Metelski | F16M 11/18 248/317 |
| 6,466,432 | B1* | 10/2002 | Beger | A61B 50/10 128/920 |
| 6,817,585 | B2* | 11/2004 | Wagner | F16M 11/10 248/324 |
| RE43,921 | E* | 1/2013 | Smed | F16M 11/10 248/124.1 |
| 10,028,651 | B2* | 7/2018 | Tesar | A61B 90/361 |
| 2001/0030683 | A1* | 10/2001 | Howell | E04B 9/006 348/61 |
| 2002/0139913 | A1* | 10/2002 | Kummerfeld | F16M 11/10 248/343 |
| 2003/0161159 | A1* | 8/2003 | Kupfer | A61B 90/35 362/402 |
| 2006/0102811 | A1* | 5/2006 | Musset | A61G 13/107 248/121 |
| 2009/0086495 | A1* | 4/2009 | Chen | A61B 90/35 362/427 |
| 2011/0303499 | A1 | 12/2011 | Chandan et al. | |
| 2014/0015948 | A1* | 1/2014 | Tam | A61B 90/30 348/77 |

FOREIGN PATENT DOCUMENTS

| | | |
|---|---|---|
| EP | 1478876 A1 | 11/2004 |
| FR | 2 662 779 A3 | 12/1991 |
| FR | 2 974 473 A1 | 10/2012 |
| JP | S36-13696 B | 4/1957 |
| JP | 2001-143522 A | 5/2001 |
| JP | 2005-522240 A | 7/2005 |
| JP | 2006-122232 A | 5/2006 |

OTHER PUBLICATIONS

JP Office Action dated Jun. 25, 2019 issued by the Japanese Patent Office in corresponding JP Application No. 2018-527782, along with English summary.

* cited by examiner

MEDICAL SUSPENSION DEVICE COMPRISING AN OFFSET ARM

CROSS REFERENCE TO RELATED APPLICATIONS

This application is the U.S. National Stage of International Application Number PCT/FR2017/050102 filed on Jan. 18, 2017, which application claims priority under 35 USC § 119 to French Patent Application No. 1650394 filed on Jan. 19, 2016. Both applications are hereby incorporated by reference in their entirety.

TECHNICAL FIELD

The field of the invention relates to a suspension device making it possible to suspend items of equipment under a support structure, such a suspension device comprising an anchor bracket designed to be anchored axially to the support structure, two distribution arms that are adjustable up and down and that are designed to carry the items of equipment, each distribution arm comprising a suspension arm having one end articulated to the anchor bracket via a pivot articulation making it possible for the suspension arm to move in rotation in a horizontal plane, and a spring arm articulated to the other end of the suspension arm so as to be inclinable vertically relative to the suspension arm, the other end of the spring arm carrying a respective item of equipment.

PRIOR ART

In a medical environment, in particular in an operating theater, medical equipment such as lighting devices, monitoring or control devices with screens and cameras, and medical fluid supplies are generally suspended from a support structure via a suspension device attached to an anchor bracket anchored to the support structure, such as a ceiling. The suspension device makes it possible to distribute the various items of equipment via distribution arms that are adjustable around a zone of use, which is most often an operating table centered in the operating theater. A distribution arm generally comprises a suspension arm connected at one end to the anchor bracket and at its other end to a spring arm that carries one or more items of medical equipment.

Documents EP 1 239 805, EP 1 442 246, and EP 1 478 876 disclose medical suspension devices, each of which supports one or more items of equipment with articulated distribution arms. Those documents describe, in particular, suspension devices fastened to an anchor bracket that is most often positioned in the center of the operating theater, in such a manner that the operating table is aligned with the anchor bracket.

It is understood by medical staff that, during an operation, moving the articulated arms carrying the various items of equipment can give rise to collisions between stationary or moving items of equipment. Such collisions can be of the type in which the spring arm comes into contact with its suspension arm, or in which a lighting dome of the lighting device fastened to an articulated arm hits a suspension arm or a spring arm of another articulated arm.

In addition, even though medical staff are often satisfied with the main function of such suspension devices, they often complain about positioning difficulties, and needing to apply large forces to manipulate the suspension devices, and they also mention that the various items of equipment can drift. Another complaint made by medical staff concerns positions for items of equipment, such as lighting devices, that are impossible to reach over the zone of use, thereby creating singularities over the zone of use.

In order to overcome those drawbacks to some extent, manufacturers of suspension devices for suspending medical equipment in an operating theater propose to anchor suspension devices on the sides of the support structure of the operating theater, so that anchor points are in the 9 o'clock 3 o'clock or 12 o'clock 6 o'clock positions relative to the operating table positioned in the center of the operating theater. Installations with anchor points of the 9 o'clock 3 o'clock type seem to procure better use of the space while also being compatible with the laminar flows that are designed initially for centralized anchoring.

Nevertheless, operating theaters are not always compatible for such installations that require a plurality of anchor points, conventional theaters making it possible for anchoring of a suspension device to be central only.

SUMMARY OF THE INVENTION

An object of the invention is thus to remedy those drawbacks by proposing a suspension device that offers the advantages of a 9 o'clock 3 o'clock arrangement of the suspension devices and that is compatible with centralized anchoring in an operating theater.

To this end, the invention provides a suspension device making it possible to suspend items of equipment under a support structure, the suspension device comprising an anchor bracket designed to be anchored axially to the support structure, two distribution arms that are adjustable up and down and that are designed to carry the items of equipment, each distribution arm comprising a suspension arm having one end articulated to the anchor bracket via a pivot articulation making it possible for the suspension arm to move in rotation in a horizontal plane, and a spring arm articulated to the other end of the suspension arm so as to be inclinable vertically relative to the suspension arm, the other end of the spring arm carrying a respective item of equipment, the suspension device being characterized in that each pivot articulation of a suspension arm is disposed at the end of an offsetting arm so as to be offset horizontally by a certain offset distance relative to the axis of the anchor bracket, which length is greater than the length of the suspension arm, and in that it further comprises connection means that secure the offsetting arm in stationary manner relative to the axis of the anchor bracket in such a manner that it remains stationary relative to the anchor bracket while the distribution arm is pivoting in the horizontal plane.

The suspension device of the invention may advantageously have the following features:
 it comprises two offsetting arms that are in mutual alignment on either side of a central point of the anchor bracket;
 the equipment is medical equipment.

With this arrangement, it is possible to create artificial offsetting of the items of equipment carried by the distribution arms (the suspension arm and the spring arm) from centralized anchoring in order to obtain a 9 o'clock 3 o'clock type configuration that is known to limit the collisions and the number of singular positions in the zone of use, while also being compatible with the laminar flows of an operating theater having centralized anchoring.

Such artificial offsetting is an inexpensive and quick solution for changing the arrangement of the items of equipment in the operating theater around the zone of use because it is compatible with an existing centralized installation, and it makes it possible to reduce the number of anchor points and to reduce the number of rotary and/or pivotal articulations compared with prior art suspension devices.

BRIEF DESCRIPTION OF THE DRAWINGS

The present invention can be better understood and other advantages appear on reading the following detailed description of embodiments given by way of non-limiting example and with reference to the accompanying drawings, in which.

DESCRIPTION OF AN EMBODIMENT

Figure 1:
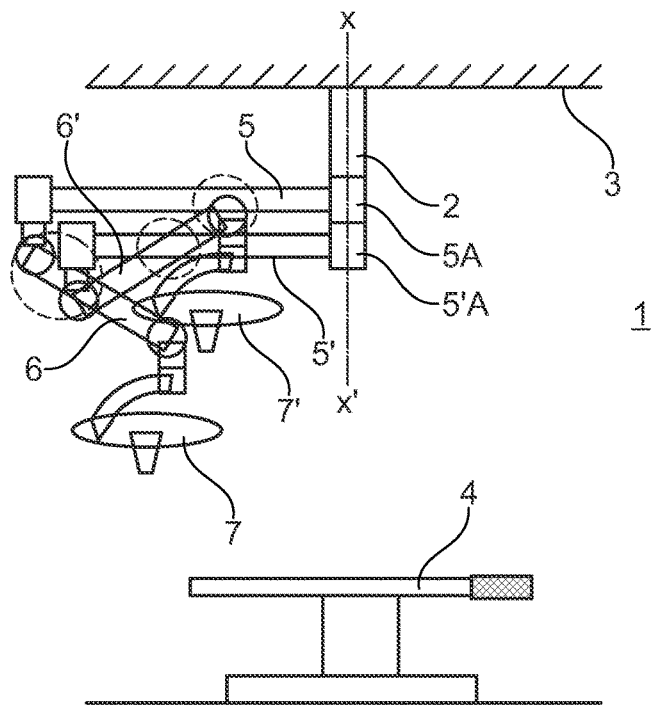
FIG. 1 is a diagrammatic view of a prior art suspension device in an operating theater.

FIG. 1 shows a prior art suspension device in an operating theater 1 with an anchor bracket 2 anchored to a support structure 3 or ceiling of the operating theater, above an operating table 4.

During a medical operation, the medical staff usually align the center of the operating table 4 so that it is vertically in register with the anchor bracket 2.

FIG. 1 shows two adjustable distribution arms, each of which is articulated relative to the anchor bracket 2, and each of which carries medical equipment 7, 7', namely medical lighting in this example, at its free end.

Instead of medical lighting 7, 7', any other electronic system could be carried, e.g. a monitoring and control system including a screen and a camera. The equipment could also be a fluid dispensing system, e.g. an intravenous drip, etc.

Conventionally, each distribution arm comprises a suspension arm 5, 5' connected at one end to the anchor bracket 2 via a pivot articulation 5A, 5'A and at the other end to a spring arm 6, 6' that, in this example, carries, at its free end, a lighting dome 7, 7' designed to form an illumination spot on a zone of an operative field that, in this example, is on the operating table 4.

The vertical axis XX' is used to represent the central axis of the anchor bracket 2, which central axis is also the axis of the pivot articulations 5A, 5'A at the ends of the suspensions arms 5, 5'.

As indicated above, with that type of suspension device, collisions can take place between the two spring arms 6, 6' of the two distribution arms or between a spring arm 6, 6' and a suspension arm 5, 5' of the same distribution arm, or of the other distribution arm.

In FIG. 1, circles in dashed lines indicate the collision zones in which collisions are most frequent.

From FIG. 1, it can be understood, for example, that the spring arm 6' interferes with the suspension arm 5' of the same distribution arm because the highest point of the spring arm 6' is higher than the lowest point of the suspension arm 5'. The lighting dome 7' can thus also collide with the suspension arm 5'.

Figure 2:
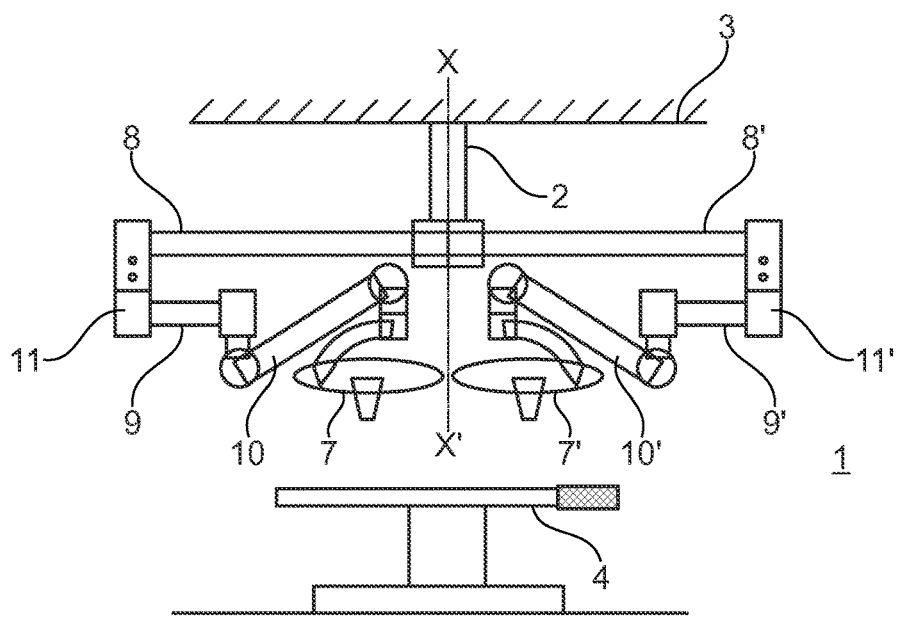
FIG. 2 is a diagrammatic view of a suspension device of the invention in an operating theater.

FIG. 2 shows the suspension device of the invention in place in the operating theater 1 with the operating table 4 aligned vertically with the anchor bracket 2 on its central axis XX'.

In the suspension device of the invention, a pivot articulation 11, 11' of a distribution arm is offset from the anchor bracket 2 (from its central axis XX') via a stationary offsetting arm 8, 8' that is interposed between the anchor bracket 2 and the articulation in question. A first end of the offsetting arm 8, 8' is connected to the anchor bracket 2, while the other end is connected to the suspension arm 9, 9' via the pivot articulation 11, 11'.

FIG. 2 shows two offsetting arms 8, 8' in mutual alignment on either side of a central point of the anchor bracket 2.

During the medical operation, each offsetting arm such as 8 or 8' is held stationary relative to the anchor bracket 2 while the distribution arm is pivoting.

As shown in FIG. 2, each distribution arm includes a suspension arm 9, 9' connected to the anchor bracket 2/offsetting arm 8, 8' via the pivot articulation 11, 11', and a spring arm 10, 10' mounted to pivot at one end of a suspension arm 9, 9' and having its other end free and carrying equipment, namely, in this example shown in FIG. 2, a medical lighting dome 7, 7'.

The stationary connection between an offsetting arm 8, 8' and the anchor bracket 2 may be of the sleeve/collar type, with disassembly and heightwise adjustment being possible before and after a medical operation. This stationary connection holds the offsetting arm 8, 8' in a position in which it is stationary relative to the anchor bracket 2 while the distribution arm is moving.

Such an offsetting arm 8, 8' is entirely suitable for being installed on an existing anchor bracket 2, in place of a suspension arm.

Instead of having two offsetting arms 8, 8' in mutual alignment, said two offsetting arms 8, 8' could be disposed in a V-shaped configuration at a fixed angle. In either configuration, they could also be superposed relative to each other.

The invention thus extends to configurations in which the suspension device has more than two distribution arms having pivot articulations 11, 11' offset from the anchor bracket 2.

Figure 3A:
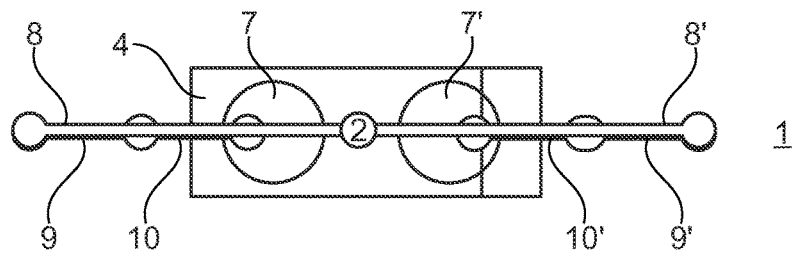
FIGS. 3A and 3B are diagrammatic views respectively showing first and second configurations of the suspension device of the invention.

In FIG. 3A, the two suspensions arms 9, 9' having the two spring arms 10, 10' are deployed in a 9 o'clock 3 o'clock configuration under the offsetting arms 8, 8'.

The two lighting domes 7, 7' face each other under the offsetting arms 8, 8'.

As can be seen in FIG. 3A and also in FIG. 2, each suspension arm 9, 9' is shorter than an offsetting arm 8, 8'.

In this situation, there is no risk of collision between the two suspension arms 9, 9', and, in addition, it is possible to move the lighting dome 7, 7' over a larger zone than with a conventional suspension device while leaving fewer zones of singularities over the operative field.

In addition, each distribution arm (suspension arm 9, 9' with spring arm 10, 10') is shorter than an offsetting arm 8, 8', and therefore the spring arms 10, 10' cannot collide with each other because each spring arm 10, 10' with a lighting dome 7, 7' has its own zone of movement above the operative field.

There is therefore no risk of collision between a spring arm 10, 10' and a suspension arm 9, 9' or between the lighting domes 7, 7'.

Figure 3B:
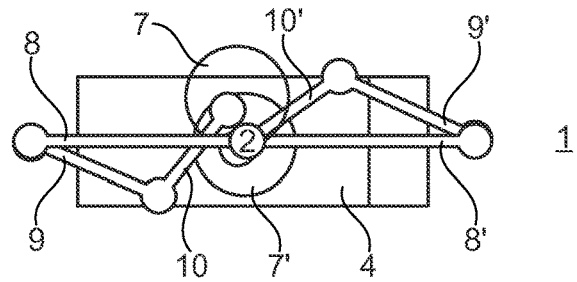

FIG. 3B shows a suspension device of the invention having two distribution arms, with two offsetting arms 8, 8' in mutual alignment, each offsetting arm 8, 8' being longer than a suspension arm 9, 9'. However, as can be seen in FIG. 3B, the spring arms 10, 10' cross over and face each other.

With this arrangement, each lighting dome 7, 7' can be positioned on either side of the operating table 4, or at the feet or at the head of a patient lying on the table.

Figure 4:
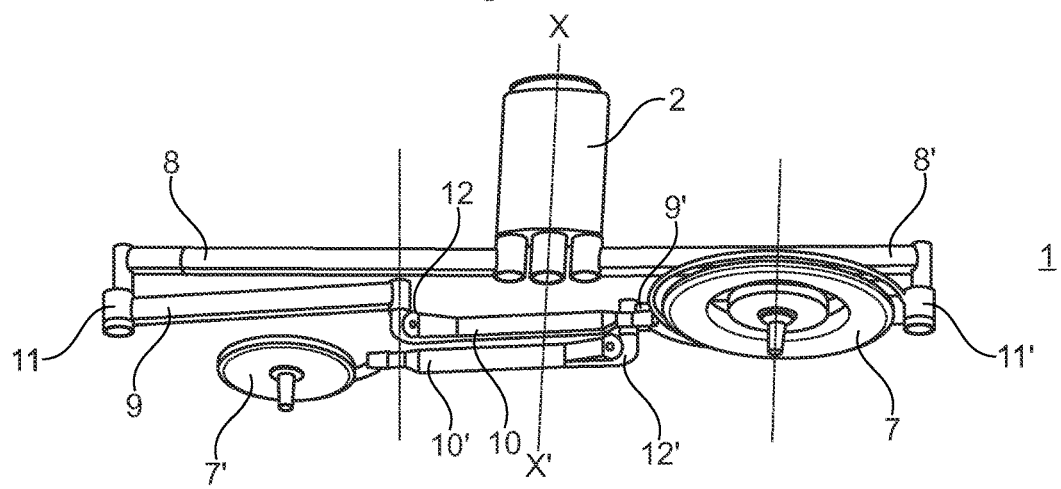
FIG. 4 is a diagrammatic perspective view of the suspension device of the invention in an operating theater.

FIG. 4 is a diagrammatic perspective view of the suspension device of the invention having two offsetting arms 8, 8'.

As indicated above, each offsetting arm 8, 8' is connected in stationary manner to the anchor bracket 2. The connection may be disassemblable or adjustable, e.g. adjustable heightwise along the axis XX'. FIG. 4 shows two connections offset from the centre of the bracket 2 and of the sleeve/collar type.

Each pivot articulation 11, 11' that connects a suspension arm 9, 9' to an offsetting arm 8, 8' may also be of the sleeve/collar type or of the hub type with it being possible to adjust the connection vertically along the axis XX'.

The articulation 12, 12' between a suspension arm 9, 9' and a spring arm 10, 10' makes it possible to incline the suspension arm 9, 9' upwards or downwards, and thus to move the dome 7, 7' further away from or closer to the operating table 4. Said articulation 12, 12' may also be a pivot articulation having a horizontal pivot axis.

Preferably, in order to avoid the risks of collision between the two suspension arms 9, 9', said suspension arms 9, 9' should not be able to reach the central axis XX' of the anchor bracket 2. Thus, each suspension arm 9, 9' is shorter than an offsetting arm 8, 8'.

In this example, the equipment is a lighting dome 7, 7' with a lighting axis arranged at the center of the lighting dome 7, 7'. In order to cover the entire zone of use of the operative field, the lighting axis of the lighting dome 7, 7' should preferably be able to be spaced apart from the axis XX' of the anchor bracket 2 by about 800 millimeters (mm)±300 mm.

The offsetting arm 8, 8' preferably has a length equivalent to at least the sum of the length of the spring arm 10, 10' and of the lighting dome up to its lighting axis.

It should be noted that the axis XX' of the anchor bracket 2 of FIG. 4 is free to receive other equipment to be suspended.

It can be understood that, in accordance with the invention, adding an offsetting arm 8, 8' to the suspension device artificially offsets the equipment 7, 7' in an operating theater 1.

This artificial offsetting of the equipment 7, 7' is compatible with the anchoring system that is centralized in an operating theater 1.

This artificial offsetting makes it easy and inexpensive to configure an operating theater 1 with suspension devices as if they were in a position of the 9 o'clock 3 o'clock type: a single anchoring point is necessary, and rotary articulations are omitted.

This arrangement with artificial offsetting offers all of the advantages procured with a 9 o'clock 3 o'clock installation. These known advantages are that collisions are limited, the items of equipment 7, 7' are moved into positions that cannot be reached by prior art suspension devices centered on the operating table 4, thereby limiting the singularities around the zone of use.

This artificial offsetting of the equipment 7, 7' in an operating theater 1 is compatible with laminar flows initially designed for centralized anchoring.

The suspension device of the invention makes it possible to reduce the forces related to manipulating the items of equipment 7, 7' fastened to the spring arms 10, 10' as is known with suspension devices in the 9 o'clock 3 o'clock position.

Naturally, the present invention is in no way limited to the above description of one of its embodiments, which can undergo modifications without going beyond the ambit of the invention.

Figure 5:
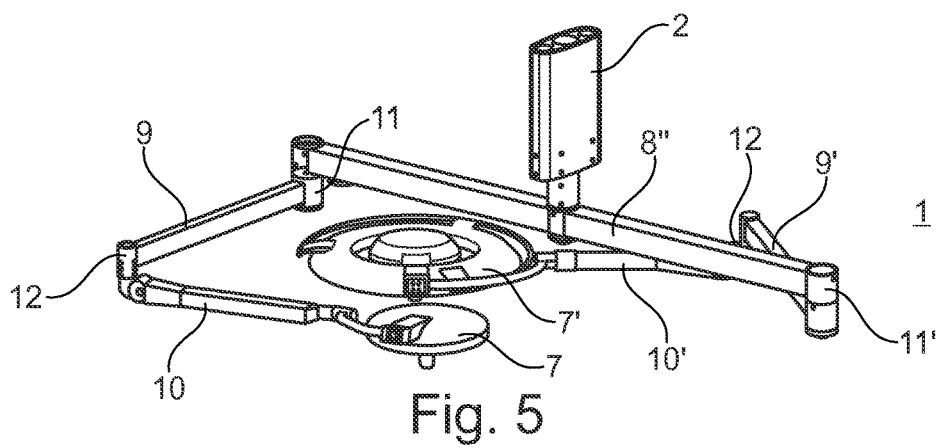
FIG. 5 is a diagrammatic perspective view of another embodiment of the suspension device of the invention in an operating theater.

For example, in another embodiment, the offsetting arms 8, 8' in mutual alignment on either side of a central point of an anchor bracket 2 as shown in FIG. 2 could be replaced with a single offsetting arm 8" fastened in its middle via a single connection to a central point of the anchor bracket 2 as shown in FIG. 5. The fastening may be of the sleeve/collar type so that it is also possible to mount, to remove, and to adjust the height of the single offsetting arm 8" before and after a medical operation.

What is claimed is:

1. A suspension device making it possible to suspend items of equipment under a support structure, said suspension device comprising:
    an anchor bracket configured to be anchored axially to said support structure,
    two distribution arms that are adjustable up and down and that are configured to carry said items of equipment, each of the distribution arm comprising a suspension arm having one end articulated to said anchor bracket via a pivot articulation making it possible for said suspension arm to move in rotation in a horizontal plane, and a spring arm articulated to the other end of said respective suspension arms so as to be inclinable vertically relative to said suspension arm, the other end of said spring arm carrying a respective item of equipment,
    wherein each of the pivot articulation of the respective suspension arm is disposed at the respective end of an offsetting arm so as to be offset horizontally by a certain offset distance relative to an axis of said anchor bracket, the offset distance is greater than a length of said suspension arm, and
    wherein said suspension device further comprises connection means that secure each of the offsetting arm in stationary manner relative to said axis of said anchor bracket in such a manner that each of the offsetting arm remains stationary relative to said anchor bracket while each of the distribution arm is pivoting in said horizontal plane.

2. The suspension device according to claim 1, wherein the offsetting arms of the suspension device are in mutual alignment on either side of a central point of said anchor bracket.

3. The suspension device according to claim 2, wherein said item of equipment is medical equipment.

4. The suspension device according to claim 1, wherein said item of equipment is medical equipment.

5. The suspension device according to claim 1, wherein said items of equipment comprise a medical light.

6. The suspension device according to claim 1, wherein the offsetting arms comprise
    two offsetting arms which are at a fixed angle extending laterally outward in opposite directions away from the anchor bracket;
        wherein each of the offsetting arm is pivotably connected to a respective suspension arm at a far end of the offsetting arm;
        wherein each of the suspension arm is shorter than the respective offsetting arm it is attached to;

wherein the suspension arms are both pivotable within a common horizontal plane; and wherein the suspension arms are mutually spaced apart by the offsetting arms such that the suspension arms cannot collide.

7. The suspension device according to claim 1, wherein the offsetting arms comprise two offsetting arms which are at a fixed angle extending laterally outward in opposite directions away from the anchor bracket;

wherein each of the offsetting arm is pivotably connected to a respective suspension arm at a far end of the offsetting arm;

wherein each of the suspension arm is shorter than the respective offsetting arm it is attached to;

wherein the suspension arms are both positioned below their respective offsetting arms, and the suspension arms are both pivotable with respect to far ends of the respective offsetting arms only within respective horizontal planes parallel to and below the offsetting arms; and wherein the suspension arms are mutually offset by the offsetting arms such that the suspension arms cannot collide.

8. The suspension device according to claim 1, wherein the offsetting arms comprise two offsetting arms that are in mutual alignment on either side of a central point of said anchor bracket;

wherein the items of equipment are lights and wherein each of the distribution arm holds one of the lights at an end thereof;

wherein each of the distribution arm is pivotably attached to a far end of a respective offsetting arm;

wherein each of the distribution arm is shorter than the corresponding offsetting arm it is attached to;

wherein the spring arms of the distribution arms cannot collide with each of the other due to offset provided by the respective offsetting arms.

9. The suspension device according to claim 1, wherein the offsetting arms comprise two offsetting arms which are at a fixed angle extending laterally outward in opposite directions away from the anchor bracket;

wherein the items of equipment are lights and wherein each of the distribution arm holds one of the lights at an end thereof;

wherein the offsetting arms are each of the longer than a collective length of the corresponding distribution arm and light, such that the lights cannot collide due to spacing provided by their respective offsetting arm.

10. The suspension device according to claim 1, wherein the offsetting arms comprise two offsetting arms extending laterally outward in opposite directions away from the anchor bracket;

wherein the offsetting arms and the suspension arms are all linear elongated arms;

wherein the suspension arms are below the corresponding offsetting arms, and are pivotable within a horizontal plane which is below and does not intersect the offsetting arms, such that the suspension arms cannot collide with the offsetting arms;

wherein it is possible to position the suspension arms so that they are parallel to their respective offsetting arms.

11. The suspension device according to claim 1, wherein the offsetting arms comprise two linear offsetting arms fixed extending laterally outward in opposite directions away from the anchor bracket, wherein the two linear arms are collectively in a form of a single continuous arm.

12. A suspension device for suspending medical equipment under a support structure, said suspension device comprising:

an anchor bracket, the anchor bracket being connectable to a ceiling;

two offsetting arms immovably fixed extending laterally outward away from the anchor bracket;

two distribution arms, each of the distribution arm being movably connected at an end of a respective offsetting arm; and two medical equipment items, each of the medical equipment item being connected to a respective distribution arm;

wherein each of the offsetting arm is longer than the corresponding distribution arm connected thereto, such that the distribution arms cannot collide.

13. A suspension device according to claim 12, wherein each distribution arm comprises a suspension arm and a spring arm;

wherein the distribution arms are each positioned below their respective offsetting arms;

wherein the distribution arms are each rotatable only within a respective horizontal plane which is below and does not intersect the respective offsetting arm, such that the distribution arms cannot collide with their corresponding offsetting arms; and wherein the spring arms are movable with respect to the corresponding distribution arms.

14. A suspension device according to claim 12, wherein the medical equipment items comprise a medical light.

15. A suspension device according to claim 12, wherein the medical equipment items are lights and wherein each of the distribution arm holds one of the lights at an end thereof; and wherein the offsetting arms are each longer than a collective length of the corresponding distribution arm and light, such that the lights cannot collide due to spacing provided by their respective offsetting arm.

16. A suspension device according to claim 12:

wherein each of the distribution arm comprises a suspension arm and a spring arm;

wherein the offsetting arms and the suspension arms are all straight elongated arms;

wherein the suspension arms are below the corresponding offsetting arms, and are pivotable within a horizontal plane which is below and does not intersect the offsetting arms, such that the suspension arms cannot collide with the offsetting arms; and wherein it is possible to position the suspension arms so that they are parallel to and directly below the respective offsetting arms.

17. A suspension device according to claim 12, wherein the offsetting arms are each linear beams extending horizontally away from the anchor bracket in opposite directions; and wherein the linear beams are in mutual alignment on opposite sides of the anchor bracket.

18. A suspension device according to claim 12, wherein the offsetting arms are each linear beams extending horizontally away from the anchor bracket in opposite directions;

wherein the offsetting beams are in mutual alignment on opposite sides of the anchor bracket;

wherein each of the distribution arm comprises a suspension arm and a spring arm; and wherein the suspension arms are each linear beams which are rotatably connected below the respective offsetting arm, such that the suspension arms cannot collide with the respective offsetting arm during movement.

19. A suspension device for suspending medical equipment under a support structure, said suspension device comprising:
- an anchor bracket, the anchor bracket being connectable to a ceiling;
- two offsetting arms fixed and extending laterally outward away from the anchor bracket, and in mutual alignment on opposite sides of the anchor bracket;
- two distribution arms, each of the distribution arm being movably connected at an end of a respective offsetting arm
- wherein each of the distribution arm comprises a suspension arm and a spring arm, with the distribution arm being movably connected to the respective offsetting arm; and
- two medical equipment items, each of the medical equipment item being connected to a respective spring arm;
- wherein each of the offsetting arm is longer than the corresponding distribution arm connected thereto, such that the distribution arms cannot collide with each other due to offset provided by the offsetting arms; and
- wherein the suspension arms are both positioned below their respective offsetting arms, and the suspension arms are both pivotable with respect to the far ends of the respective offsetting arms within respective horizontal planes below the offsetting arms such that the suspension arms and offsetting arms cannot collide.

20. A suspension device according to claim 19, wherein the spring arms are vertically pivotable with respect to the corresponding suspension arm; and
- wherein the medical equipment items are lights, with the lights being connected at an end of each of the spring arm respectively.

* * * * *